United States Patent [19]

Stern et al.

[11] Patent Number: 5,252,737

[45] Date of Patent: Oct. 12, 1993

[54] PROCESS FOR PREPARING N-ALIPHATIC SUBSTITUTED P-PHENYLENEDIAMINES

[75] Inventors: Michael K. Stern, University City; Brian K-M. Cheng, St. Charles, both of Mo.

[73] Assignee: Monsanto Company, St. Louis, Mo.

[21] Appl. No.: 887,981

[22] Filed: May 22, 1992

[51] Int. Cl.$^5$ .................. C07C 209/00; C07C 209/36

[52] U.S. Cl. .................. 544/392; 546/232; 562/433; 562/437; 564/305; 564/367; 564/397; 564/398; 564/416; 564/420; 564/422; 564/423; 564/431; 564/441; 564/443

[58] Field of Search .................. 544/392; 546/232; 562/433, 437; 564/305, 367, 397, 398, 416, 420, 422, 423, 431, 441, 443

[56] References Cited

U.S. PATENT DOCUMENTS

| | | | |
|---|---|---|---|
| 3,414,616 | 12/1968 | Summers et al. | 260/566 |
| 3,847,990 | 11/1974 | Blahak | 260/576 |
| 4,122,118 | 10/1978 | George et al. | 260/576 |
| 4,140,716 | 2/1979 | Maender et al. | 260/562 R |
| 4,155,936 | 5/1979 | Sturm | 260/576 |
| 4,178,315 | 12/1979 | Zengel et al. | 260/647 |
| 4,187,248 | 2/1980 | Merten et al. | 260/576 |
| 4,187,249 | 2/1980 | Merten et al. | 260/576 |
| 4,196,146 | 4/1980 | Merten et al. | 260/576 |
| 4,209,463 | 6/1980 | Maender et al. | 260/576 |
| 4,404,401 | 9/1983 | Zengel et al. | 564/416 |
| 4,463,191 | 7/1984 | D'Sidocky et al. | 564/398 |
| 4,479,008 | 10/1984 | Batorewicz et al. | 564/433 |
| 4,518,803 | 5/1985 | Batorewicz et al. | 564/410 |
| 4,614,817 | 9/1986 | Maender et al. | 564/406 |
| 4,670,595 | 6/1987 | Podder et al. | 564/406 |
| 4,683,332 | 7/1987 | Sturm | 564/414 |
| 4,760,186 | 7/1988 | Solodar | 564/415 |
| 4,900,868 | 2/1990 | Merten et al. | 564/398 |

FOREIGN PATENT DOCUMENTS

| | | |
|---|---|---|
| 293999 | 12/1988 | European Pat. Off. . |
| 1440767 | 6/1976 | United Kingdom . |

OTHER PUBLICATIONS

Huisgen et al., Ann. Chem., 594 (1955) pp. 159–165.

Ayyangar, N. R. et al., "A Novel Reaction of Acetanilide with Nitrobenzene in DMSO-An Unusual Solvent Assisted Regioselective Aromatic Nucleophilic Substitution", Tetrahedron Letters, vol. 31, No. 22, pp. 3217–3220 (1990).

Wohl, A., "Toward the Knowledge of the Reaction Between Nitrobenzene and Aniline in the Presence of Alkali", Chemische Berichte, 36, pp. 4135–4138 (1903).

Wohl, A. and Aue, W., Chemische Berichte, 34, pp. 2442–2450 (1901).

Banerjee, A. A. and Mukesh, D., "Heterogeneous Catalytic Transfer Hydrogenation of 4-Nitrodiphenylamine to p-Phenylenediamines", J. Chem. Soc., Chem. Comm., 18, 1275–1276 (1988).

Rylander, W. P., "Catalytic Hydrogenation in Organic Synthesis", Academic Press, p. 299 (1979).

Jencks, W. P., J. Am. Chem. Soc., 92, 3201–3202 (1970).

Katritzky, A. R. and Laurenzo, K. S., "Alkylaminonitrobenzenes by Vicarious Nucleophilic Amination with 4-(Alkylamino)-1,2,4-triazoles", J. Org. Chem., 53, 3978–3982 (1988).

Bradley, W. and Robinson, R., "Kationoid Reactivity of Aromatic Compounds. Part I", J. Chem. Soc., pp. 1254–1263 (1932).

Montmollin, G. and Montmollin, M., Helv. Chim. Acta, 6, 94 (1924).

Primary Examiner—Richard L. Raymond
Attorney, Agent, or Firm—Kenneth D. Goetz

[57] ABSTRACT

A process for preparing N-aliphatic substituted p-phenylenediamine intermediates is provided which comprises contacting an aliphatic amine or substituted aliphatic amine derivative and nitrobenzene in the presence of a suitable solvent system, and reacting the aliphatic amine or substituted aliphatic amine derivative and nitrobenzene in the presence of a suitable base and a controlled amount of protic material at a suitable temperature in a confined reaction zone. In one embodiment, the N-aliphatic substituted p-phenylenediamine intermediates are reduced to N-aliphatic substituted p-phenylenediamines and the N-aliphatic substituted p-phenylenediamines can be reductively alkylated to N'-alkylated, N-aliphatic substituted p-phenylenediamines. In another embodiment of the invention, N-aliphatic substituted p-phenylenediamine intermediates are reductively alkylated to N'-alkylated, N-aliphatic substituted p-phenylenediamines.

66 Claims, No Drawings

PROCESS FOR PREPARING N-ALIPHATIC SUBSTITUTED P-PHENYLENEDIAMINES

BACKGROUND OF THE INVENTION

This invention relates to the production of N-aliphatic substituted p-phenylenediamine intermediates. In one aspect, this invention relates to the production of N-aliphatic substituted p-phenylenediamines. In another aspect, this invention relates to the production of N'-alkylated, N-aliphatic substituted p-phenylenediamines useful as antioxidants or antiozonants.

It is known to prepare dialkyl substituted p-phenylenediamines by the reaction of a p-halonitrobenzene with ammonia to produce p-nitroaniline followed by reductive alkylation of the p-nitroaniline. This process involves a nucleophilic aromatic substitution mechanism wherein the ammonia replaces halide to produce the p-nitroaniline. This process is disadvantageous in that the halide that is displaced is corrosive to the reactors and appears in the waste stream and must therefore be disposed of at considerable expense. Therefore, a nonhalide route to N-aliphatic substituted p-phenylenediamines and the alkylated products thereof would provide significant advantages over current technology and result in a more efficient and economic commercial process.

The process of the invention is such a nonhalide route to N-aliphatic substituted p-phenylenediamines and the alkylated products thereof and therefore eliminates the expensive halide removal from the waste stream as well as corrosion problems caused by the halide.

SUMMARY OF THE INVENTION

It is an object of the invention to provide a process for producing N-aliphatic substituted p-phenylenediamine intermediates for use in the production of N-aliphatic substituted p-phenylenediamines and N'-alkylated, N-aliphatic substituted p-phenylenediamines. It is a further object of the invention to provide an efficient and economic process to produce N-aliphatic substituted p-phenylenediamine intermediates and products thereof that is commercially viable. It is a further object of the invention to provide a process for producing N-aliphatic substituted p-phenylenediamines for use as intermediates to antioxidants. It is a still further object of the invention to provide a process for producing N'-alkylated, N-aliphatic substituted p-phenylenediamines for use as antioxidants or antiozonants.

According to the invention, a process for preparing aliphatic substituted p-phenylenediamine intermediates is provided which comprises contacting an aliphatic amine or substituted aliphatic amine derivative and nitrobenzene in the presence of a suitable solvent system, and reacting the aliphatic amine or substituted aliphatic amine derivative and nitrobenzene in the presence of a suitable base and a controlled amount of protic material at a suitable temperature in a confined reaction zone. In one embodiment of the invention, the amount of protic material present during the reaction of aliphatic amine or substituted aliphatic amine derivative and nitrobenzene is controlled by having a desiccant present during the reaction. In another embodiment, the amount of protic material present during the reaction of aliphatic amine or substituted aliphatic amine derivative and nitrobenzene is controlled by continuously removing protic material by distillation.

Further according to the invention, a process for preparing N-aliphatic substituted p-phenylenediamines is provided which comprises reducing the N-aliphatic substituted p-phenylenediamine intermediates prepared according to the invention. In one embodiment, the N-aliphatic substituted p-phenylenediamine is reductively alkylated to produce N'-alkylated, N-aliphatic substituted p-phenylenediamine.

Further according to the invention, a process for preparing N'-alkylated, N-aliphatic substituted p-phenylenediamines is provided which comprises reductively alkylating the N-aliphatic substituted p-phenylenediamine intermediates prepared according to the invention.

DETAILED DESCRIPTION OF THE INVENTION

The invention relates to a process for preparing N-aliphatic substituted p-phenylenediamine intermediates comprising:

(a) contacting an aliphatic amine or substituted aliphatic amine derivative and nitrobenzene in the presence of a suitable solvent system, and (b) reacting the aliphatic amine or substituted aliphatic amine derivative and nitrobenzene in the presence of a suitable base and a controlled amount of protic material at a suitable temperature in a confined reaction zone.

For producing N-aliphatic substituted p-phenylenediamine, the process of the invention further comprises:

(c) reducing the reaction product of (b) under conditions which produce N-aliphatic substituted p-phenylenediamine.

For producing N'-alkylated, N-aliphatic substituted p-phenylenediamines from N-aliphatic substituted p-phenylenediamines, the process of the invention further comprises:

(d) reductively alkylating the N-aliphatic substituted p-phenylenediamine to produce N'-alkylated, N-aliphatic substituted p-phenylenediamine.

For producing N'-alkylated, N'-aliphatic substituted p-phenylenediamines from N-aliphatic substituted p-phenylediamine intermediates, the process of the invention further comprises:

(c') reductively alkylating the reaction product of (b) to produce N'-alkylated, N-aliphatic substituted p-phenylenediamine.

As used herein, the term "N-aliphatic substituted p-phenylenediamine intermediates" means N-aliphatic substituted, 4-nitroaniline, N-aliphatic substituted, 4-nitrosoaniline (also referred to as N-aliphatic substituted, p-nitrosoaniline), the substituted derivatives thereof and the salts thereof. Thus, reference to "one or more N-aliphatic substituted p-phenylenediamine intermediates" refers to one or both of the neutral compounds, i.e., those that are not in the form of a salt, and/or the salt of one or both of such compounds. The salt is produced in the reaction mixture from reaction of the 4-nitro and/or 4-nitroso products with the base. Thus, the reaction mixtures produced in the process of the invention can include one of the compounds or salts or any combination thereof depending on the specific reaction conditions and specific aliphatic amine selected.

Aliphatic amines or substituted aliphatic amine derivatives that can be employed according to the invention are compounds selected from the group consisting of compounds having the formula X-R-NH-R'-Y and compounds having the formula:

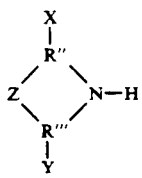

wherein R is selected from the group consisting of alkylene, alkenylene, cycloalkylene and cycloalkenylene groups, R' is selected from the group consisting of a direct bond, alkylene, alkenylene, cycloalkylene and cycloalkenylene groups, R" and R''' are independently selected from the group consisting of alkylene and alkenylene groups, Z is selected from the group consisting of a direct bond, —NH—, —N(R$_1$)—, O— and —S—, and X and Y are independently selected from the group consisting of hydrogen, halides, —NO$_2$, —NH$_2$, aryl groups, alkoxy groups, —SO$_3$R$_1$, —SO$_3$H, —OH, —COH, —COOH, and alkyl, aryl, arylalkyl or alkylaryl groups containing at least one —NH$_2$ group wherein R$_1$ is an alkyl group. Halides are selected from the group consisting of chloride, bromide and fluoride.

Examples of aliphatic amines and substituted aliphatic amine derivatives include, but are not limited to, cyclohexyl amine, 2-butylamine, isopropylamine, 2-hexylamine, 2-heptylamine, 1,4-dimethylpentylamine, 1-methylheptylamine, 1-ethyl-3-methylpentylamine, 1,3-methylbutylamine, octylamine, piperidine, piperazine, hexamethylenediamine, 2-amino-1-butanol, 6-aminohexanoic acid and mixtures thereof.

The molar ratio of aliphatic amine or substituted aliphatic amine derivative to nitrobenzene can vary from a large excess of nitrobenzene to a large excess of aliphatic amine or substituted aliphatic amine derivative. When nitrobenzene is used as the suitable solvent for the reaction, nitrobenzene is preferably present in a large excess relative to the aliphatic amine or substituted aliphatic amine derivative. When aliphatic amine or substituted aliphatic amine derivative is used as the suitable solvent for the reaction, aliphatic amine or substituted aliphatic amine derivative is preferably present in a large excess relative to the nitrobenzene. When nitrobenzene, aliphatic amine or substituted aliphatic amine derivative is not used as the solvent for the reaction, the molar ratio of aliphatic amine or substituted aliphatic amine derivative to nitrobenzene can vary over a wide range, but is preferably about 1:1.

Suitable solvent systems include, but are not limited to, solvents such as, for example, nitrobenzene, aliphatic amines or substituted aliphatic amine derivatives, dimethylsulfoxide, dimethylformamide, N-methyl-2-pyrrolidone, pyridine, N-methylaniline, chlorobenzene and mixtures thereof. As described in more detail below, solvent mixtures can be utilized wherein one or more of the suitable solvents and another solvent, such as a controlled amount of a protic solvent, are combined. Examples of protic solvent include, but are not limited to, methanol, water and mixtures thereof.

Suitable bases include, but are not limited to, organic and inorganic bases such as alkali metals, such as sodium metal, alkali metal hydrides, hydroxides and alkoxides, such as sodium hydride, lithium hydroxide, sodium hydroxide, cesium hydroxide, potassium hydroxide, potassium t-butoxide, and the like, including mixtures thereof. Other acceptable base materials include, but are not limited to, phase transfer catalysts in conjunction with a suitable base source such as tetrasubstituted ammonium hydroxides or halides wherein each substituent is independently selected from alkyl, aryl or arylalkyl groups wherein the alkyl, aryl and arylalkyl groups preferably have 1 to about 18 carbon atoms, including tetraalkyl ammonium hydroxides, e.g., tetramethyl ammonium hydroxide, tetraalkyl ammonium halides, e.g., tetrabutyl ammonium chloride, aryl, trialkyl ammonium hydroxides, e.g., phenyltrimethylammonium hydroxide, arylalkyl, trialkyl ammonium hydroxides, e.g., benzyltrimethyl ammonium hydroxide, alkyl substituted diammonium hydroxides, e.g., bis-dibutylethylhexamethylene diammonium hydroxide, and other combinations of phase transfer catalysts and suitable bases such as suitable bases in conjunction with aryl ammonium salts, crown ethers and the like, and amine bases such as lithium, bis(trimethysilyl) amide, and the like, including mixtures thereof. Preferred materials for use as bases are tetraalkylammonium hydroxides such as tetramethylammonium hydroxide or tetrabutylammonium hydroxide.

Preferably, the base is added to the aliphatic amine or substituted aliphatic amine derivative to produce a mixture which is then combined with the nitrobenzene. Alternatively, the base can be added after the aliphatic amine or substituted aliphatic amine derivative and nitrobenzene have been combined. Addition of materials can be above or below surface addition.

The amount of base employed according to the invention can be conveniently expressed in terms of a molar ratio of suitable base to aliphatic amine or substituted aliphatic amine derivative. Broadly, the molar ratio of base to aliphatic amine or substituted aliphatic amine derivative will be about 1:1 to about 10:1, preferably about 1:1 to about 4:1, and most preferably about 1:1 to about 2:1.

The reaction is conducted at a suitable temperature which can vary over a wide range. For example, the temperature can fall within a range of from about 10° C. to about 150° C., such as from about 20° C. to about 100° C., preferably from about 30° C. to about 90° C. A most preferred temperature for conducting the reaction of the invention is from about 60° C. to about 80° C.

Control of the amount of protic material present in the reaction is important. The amount of protic material employed according to the invention can be conveniently expressed in terms of a molar ratio based on the amount of base present at the beginning of the reaction of aliphatic amine or substituted aliphatic amine derivative and nitrobenzene. Broadly, the molar ratio of protic material to base will be 0:1 to about 5:1, preferably 0:1 to about 4:1, more preferably 0:1 to about 3:1, and most preferably 0:1 to about 1:1. Thus, the present reaction could be conducted under anhydrous conditions. As used herein, the term "controlled amount" of protic material is an amount up to that which inhibits the reaction of aliphatic amine or substituted aliphatic amine derivative with nitrobenzene. The upper limit for the amount of protic material present in the reaction varies with the solvent. In addition, the amount of protic material tolerated will vary with the type of base, amount of base, and base cation, used in the various solvent systems. However, it is within the skill of one in the art, utilizing the teachings of the present invention, to determine the specific upper limit of the amount of protic material for a specific solvent, type and amount of base, base cation and the like. The minimum amount of protic material necessary to maintain selectivity of the desired products will also depend upon the solvent, type and amount of base, base cation and the like, that is utilized and can also be determined by one skilled in the art.

Since the amount of protic material present in the reaction is important, it is possible to reduce the amount of protic material present as much as possible and then add back to the reaction the desired amount. Protic materials that can be utilized to add back to the reaction are known to those skilled in the art and include, but are not limited to, water, methanol and the like, and mixtures thereof. Methods for measuring the amount of protic material and for reducing the amount of protic material as much as possible are well known in the art. For example, the amount of water present in certain reagents can be determined by utilizing a Karl-Fischer apparatus, and the amount of water can be reduced through distillation and/or drying under reduced pressure, drying in the presence of $P_2O_5$ and other agents, azeotropic distillation utilizing, for example, aniline, and the like, including combinations thereof.

In one embodiment for controlling the amount of protic material during the reaction of aliphatic amine or substituted aliphatic amine derivative and nitrobenzene, a desiccant is added so as to be present during the reaction of aliphatic amine or substituted aliphatic amine derivative and nitrobenzene. For example, when the protic material is water, the desiccant removes water present during the reaction of aliphatic amine or substituted aliphatic amine derivative and nitrobenzene and results in higher conversion of nitrobenzene and yields of N-aliphatic substituted p-phenylenediamine intermediates. As used herein, desiccant is a compound present during the reaction of aliphatic amine or substituted aliphatic amine derivative and nitrobenzene in addition to the suitable base used. Examples of suitable desiccants include, but are not limited to, anhydrous sodium sulfate, molecular sieves, such as types 4A, 5A, and 13X available from the Union Carbide Corporation, calcium chloride, tetramethylammonium hydroxide dihydrate, anhydrous bases such as KOH and NaOH, and activated alumina.

In another embodiment for controlling the amount of protic material during the reaction of aliphatic amine or substituted aliphatic amine derivative and nitrobenzene, protic material is continuously removed from the reaction mixture by distillation. If the protic material present forms an azeotrope with one of the compounds in the reaction mixture, the protic material can be removed by continuous azeotropic distillation of protic material utilizing the azeotrope. The continuous removal of protic material allows the use of lower amounts of base in the reaction of aliphatic amine or substituted aliphatic amine derivative and nitrobenzene while achieving higher conversion of nitrobenzene and higher yields of N-aliphatic substituted p-phenylenediamine intermediates.

The reaction can be conducted under aerobic conditions for all aliphatic amines or substituted aliphatic amine derivatives. Under aerobic conditions, the reaction is conducted essentially as described above in the reaction zone which is exposed to oxygen, usually by exposure to air. Under aerobic conditions, the pressure at which the reaction is conducted can vary and the optimal pressure, as well as the optimal combination of pressure and temperature, are easily determined by one skilled in the art. For example, the reaction can be conducted at room temperature and at a pressure ranging from about 10 psig to about 250 psig, such as from about 14 psig to about 150 psig. The reaction can be conducted under anaerobic conditions for aliphatic amines or substituted aliphatic amine derivatives having the formula X—R—NH$_2$ wherein X and R are as defined herein. Under anaerobic conditions, the reaction can be conducted at atmospheric pressure or reduced or elevated pressures, in the presence of an inert gas such as, for example, nitrogen or argon. Optimal conditions for a particular set of reaction parameters, such as temperature, base, solvent and the like, are easily determined by one skilled in the art utilizing the teaching of the present invention.

The N-aliphatic substituted p-phenylenediamine intermediates and/or their salts can be reduced to N-aliphatic substituted p-phenylenediamines. The neutral compounds can be generated from the salts utilizing water and/or an acid. Alternatively, the salts can be reduced. These reductions can be carried out by any of many known reductive processes, such as using a hydride source, e.g., sodium borohydride in conjunction with palladium- or platinum-on-carbon catalysts. Preferably, this reduction is conducted by a catalytic reduction wherein hydrogenation is effected under hydrogen pressure in the presence of platinum- or palladium-on-carbon, nickel, and the like. This hydrogenation process is described in detail in "Catalytic Hydrogenation in Organic Synthesis", P. N. Rylander, Academic Press, N.Y., page 299 (1979), which is incorporated by reference herein. The hydrogenation can be conducted in a variety of solvents including, but not limited to, toluene, xylene, aniline, ethanol, dimethylsulfoxide, water and mixtures thereof. Preferably, the hydrogenation is conducted utilizing a platinum-on-carbon or palladium-on-carbon catalyst in a suitable solvent such as, for example, either ethanol, aniline, or dimethylsulfoxide, mixtures thereof, or mixtures which include water as the solvent and a hydrogen pressure of from 100 psig H$_2$ to about 340 psig H$_2$ at a temperature of about 80° C.

Reductive alkylation of N-aliphatic substituted p-phenylenediamines to produce antioxidants or antiozonants can be conducted by any one of several well-known methods. See, for example, U.S. Pat. No. 4,900,868. Preferably, N-aliphatic substituted p-phenylenediamines and a suitable ketone or aldehyde are reacted in the presence of hydrogen and platinum-on-carbon as catalysts. Suitable ketones include, but are not limited to, methylisobutyl ketone (MIBK), acetone, methylisoamyl ketone and 2-octanone. It should be noted that reduction of N-aliphatic substituted p-phenylenediamines and alkylation of the reduced material can be conducted in the same reaction vessel utilizing the ketone as a solvent. See, for example, U.S. Pat. No. 3,414,616, U.S. Pat. No. 4,463,191, and Bannerjee et al, *J. Chem. Soc. Chem. Comm.*, 18, pp 1275–76 (1988).

Contemplated equivalents of the reactants and reagents set forth above are reactants and reagents otherwise corresponding thereto and having the same general properties wherein one or more of the various groups, e.g., —NO$_2$ are simple variations. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the process of this invention. Occasionally, the reaction conditions may not be applicable as specifically described to each reactant and reagent within the disclosed scope. For example, certain suitable bases may not be as soluble in one solvent as they are in other solvents. The reactants and reagents for which this occurs will be readily recognized by those skilled in the art. In all such cases, either the reactions can be successfully performed by conventional modifications known to those skilled in the art, e.g., by appropriate adjustments in temperature, pressure and the like, by changing to alternative conventional reagents such as other solvents or other bases, by routine modification of reaction conditions, and the like, or other reactions disclosed herein or otherwise conventional, will be applicable to the process of this invention. In all preparative methods, all starting materials are known or are readily preparable from known starting materials.

EXAMPLES

Materials and Methods: Amines and nitrobenzene were purchased from Aldrich Chemical and were used without further purification. Solvents were purchased from Aldrich Chemical and were anhydrous grade. The tetramethylammonium hydroxide was purchased as the pentahydrate.

HPLC Assay: Reverse phase HPLC was used to analyze the reaction mixtures. A 5 μm Beckman/Altex Ultrasphere-ODS (4.6×150 mm) column was employed using a binary gradient pump system. Absorption in the UV was monitored at 254 nm.

A Waters 600 series HPLC equipped with a Vydac 201HS54 (4.6×250 mm) column and UV detection at 254 nm was used to monitor all reactions. The external standard method was utilized in all the analyses. Authentic samples of products to be used as standards were prepared by known literature methods. All yields are based on nitrobenzene.

| | Elution Gradient | |
|---|---|---|
| Time (min.) | % Solvent A (Water) | % Solvent B (40% Methanol in ACN) |
| 0 | 75 | 25 |
| 35 | 20 | 80 |
| 40 | 0 | 100 |
| 45 | 0 | 100 |
| 46 | 75 | 25 |
| 55 | 75 | 25 |

EXAMPLE 1

This example illustrates the reaction of a cycloalkyl primary amine with nitrobenzene.

A solution of 0.99 g of cyclohexylamine, 1.81 g of tetramethylammonium hydroxide dihydrate and 2 ml of DMSO was heated to 70° C. under nitrogen then 0.5 ml of nitrobenzene was added dropwise via a syringe. The solution was stirred for 4 hours. An aliquot was taken out for HPLC analysis. Yield of N-(4-nitrophenyl)cyclohexylamine 18% and of N-4-(nitrosophenyl)cyclohexylamine 8%.

EXAMPLE 2

This example illustrates the reaction of an branched alkyl primary amine with nitrobenzene.

A) A solution of 0.55 g of 2-heptylamine, 1.8 g of tetramethylammonium hydroxide dihydrate and 2 ml of DMSO was heated to 70° C. under nitrogen then 0.5 ml of nitrobenzene was added dropwise via a syringe. The solution was stirred for 4 hours. An aliquot was removed for HPLC analysis. Yield of N-(4-nitrophenyl)-2-heptylamine 4% and of N-4-(nitrosophenyl)-2-heptylamine 4%.

B) A solution of 5 g of 2-butylamine, 1.81 g of tetramethylammonium hydroxide dihydrate and 2 ml of DMSO was heated to 70° C. under nitrogen then 0.5 ml of nitrobenzene was added dropwise via a syringe. The solution was stirred for 4 hours. An aliquot was taken out for HPLC analysis. Yield of N-4-(nitrosophenyl)-2-butylamine 4% and of N-4-(nitrophenyl)-2-butylamine 4%.

EXAMPLE 3

This example illustrates the reaction of a secondary amine with nitrobenzene.

Piperidine (3 mL), 0.9 g of tetramethylammonium hydroxide dihydrate and 3 ml of toluene was stirred at 80° C. for 15 minutes then the toluene and water was removed at 750 mmHg/80° C. Nitrobenzene (0.5 mL) was added slowly via a syringe and the solution was stirred under air for 4 hours at 80° C. An aliquot was taken out for HPLC analysis. Yield of N-4-(nitrophenyl)-piperidine 18%.

That which is claimed is:

1. A process for preparing N-aliphatic substituted p-phenylenediamine intermediates comprising:
   (a) contacting an aliphatic amine or substituted aliphatic amine derivative and nitrobenzene in the presence of a suitable solvent system, and
   (b) reacting the aliphatic amine or substituted aliphatic amine derivative and nitrobenzene in the presence of a suitable base and a controlled amount of protic material at a suitable temperature in a confined reaction zone.

2. The process of claim 1 wherein said aliphatic amine and said substituted aliphatic amine derivative are selected from the group consisting of compounds having the formula X—R—NH—R'—Y and compound having the formula:

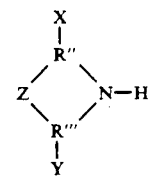

wherein R is selected from the group consisting of alkylene, alkenylene, cycloalkylene and cycloalkenylene groups, R' is selected from the group consisting of a direct bond, alkylene, alkenylene, cycloalkylene and cycloalkenylene groups, R" and R''' are independently selected from the group consisting of alkylene and alkenylene groups, Z is selected from the group consisting of a direct bond, —NH—, —N(R$_1$)—, —O— and S—, and X and Y are independently selected from the group consisting of hydrogen, halides, —NO$_2$, —NH$_2$, aryl groups, alkoxy groups, —SO$_3$R$_1$, —SO$_3$H, —OH, —COH, —COOH, and alkyl, aryl, arylalkyl or alkylaryl groups containing at least one —NH$_2$ group, wherein R$_1$ is an alkyl group and halides are selected from the group consisting of chloride, bromide and fluoride.

3. The process of claim 1 wherein said aliphatic amine and said substituted aliphatic amine derivatives are selected from the group consisting of cyclohexylamine, 2-butylamine, isopropylamine, 2-hexylamine, 2-heptylamine, 1,4-dimethylpentylamine, 1-methylheptylamine, 1-ethyl-3-methylpentylamine, 1,3-dimethylbutylamine, octylamine, piperidine, piperazine, 2-amino-1-propanol, 2-amino-1-butanol, hexamethylenediamine and 6-amino-hexanoic acid.

4. The process of claim 1 wherein said suitable solvent system includes a solvent selected from the group consisting of nitrobenzene, aliphatic amine, dimethylsulfoxide, dimethylformamide, N-methyl-2-pyrrolidone, pyridine, toluene, hexane, ethyleneglycoldimethylether, diisopropylethylamine, chlorobenzene and mixtures thereof.

5. The process of claim 4 wherein said solvent is selected from the group consisting of nitrobenzene, N-methyl-2-pyrrolidone, pyridine, dimethylsulfoxide, dimethylformamide and toluene.

6. The process of claim 4 wherein said suitable solvent system includes a protic solvent.

7. The process of claim 6 wherein said protic solvent is selected from the group consisting of methanol, water and mixtures thereof.

8. The process of claim 1 wherein the molar ratio of said protic material to said suitable base is 0:1 to about 5:1 and the molar ratio of said suitable base to said aliphatic amine or substituted aliphatic mine derivative is about 1:1 to about 10:1.

9. The process of claim 1 wherein said suitable temperature is from about 10° C. to about 150° C.

10. The process of claim 1 wherein said suitable base is selected from the group consisting of organic and inorganic bases.

11. The process of claim 10 wherein said organic and inorganic bases are selected from the group consisting of alkali metals, alkali metal hydrides, alkali metal hydroxides, alkali metal alkoxides, phase transfer catalyst in conjunction with a base source, amines, crown ethers in conjunction with a base source, alkyl magnesium halides, and mixtures thereof.

12. The process of claim 1 wherein said base is selected from the group consisting of an aryl ammonium, alkyl ammonium, aryl/alkyl ammonium and alkyl diammonium salt in conjunction with a base source.

13. The process of claim 1 wherein said base is combined with said aliphatic amine or substituted aliphatic amine derivative to form a mixture, which mixture is then contacted with nitrobenzene.

14. The process of claim 1 wherein said aliphatic amine or substituted aliphatic amine derivative and nitrobenzene are contacted to form a mixture to which said base is added.

15. The process of claim 1 wherein said solvent is nitrobenzene and said base is a tetraalkyl ammonium hydroxide.

16. The process of claim 1 wherein said aliphatic amine or substituted aliphatic amine derivative and nitrobenzene are reacted under aerobic conditions.

17. The process of claim 2 wherein said aliphatic amine or substituted aliphatic amine derivative is represented by the formula X—R—NH$_2$ and said aliphatic amine or substituted aliphatic amine derivative and nitrobenzene are reacted under anaerobic conditions.

18. The process of claim 1 wherein a desiccant is present during step (b) to control the amount of protic material present during the reaction of aliphatic amine or substituted aliphatic amine derivative and nitrobenzene.

19. The process of claim 18 wherein said desiccant is selected from the group consisting of anhydrous sodium sulfate, molecular sieves, calcium chloride, tetramethylammonium hydroxide dihydrate, anhydrous potassium hydroxide, anhydrous sodium hydroxide and activated alumina.

20. The process of claim 1 wherein the amount of protic material in step (b) is controlled by the continuous distillation of said protic material.

21. A process for preparing N-aliphatic substituted p-phenylenediamine comprising:
(a) contacting an aliphatic amine or substituted aliphatic amine derivative and nitrobenzene in the presence of a suitable solvent system,
(b) reacting the aliphatic amine or substituted aliphatic amine derivative and nitrobenzene in the presence of a suitable base and a controlled amount of protic material at a suitable temperature in a confined reaction zone, and
(c) reducing the reaction product of (b) under conditions which produce N-aliphatic substituted p-phenylenediamine.

22. The process of claim 21 wherein said aliphatic amine and said substituted aliphatic amine derivative are selected from the group consisting of compounds having the formula X—R—NH—R'—Y and compounds having the formula:

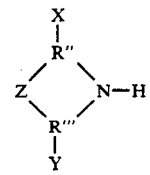

wherein R is selected from the group consisting of alkylene, alkenylene, cycloalkylene and cycloalkenylene groups, R' is selected from the group consisting of a direct bond, alkylene, alkenylene, cycloalkylene and cycloalkenylene groups, R" and R''' are independently selected from the group consisting of alkylene and alkenylene groups, Z is selected from the group consisting of a direct bond, —NH—, —N(R$_1$)—, —O— and S—, and X and Y are independently selected from the group consisting of hydrogen, halides, —NO$_2$, —NH$_2$, aryl groups, alkoxy groups, —SO$_3$R$_1$, —SO$_3$H, —OH, —COH, —COOH, and alkyl, aryl, arylalkyl or alkylaryl groups containing at least one —NH$_2$ group, wherein R$_1$ is an alkyl group and halides are selected from the group consisting of chloride, bromide and fluoride.

23. The process of claim 22 wherein said aliphatic amine and said substituted aliphatic amine derivatives are selected from the group consisting of cyclohexylamine, 2-butylamine, isopropylamine, 2-hexylamine, 2-heptylamine, 1,4-dimethylpentylamine, 1-methylheptylamine, 1-ethyl-3-methylpentylamine, 1,3-dimethylbutylamine, octylamine, piperidine, piperazine, 2-amino-1-propanol, 2-amino-1-butanol, hexamethylenediamine and 6-amino-hexanoic acid.

24. The process of claim 21 wherein said suitable solvent system includes a solvent selected from the group consisting of nitrobenzene, aliphatic amine, dimethylsulfoxide, dimethylformamide, N-methyl-2-pyrrolidone, pyridine, toluene, hexane, ethyleneglycoldimethylether, diisopropylethylamine, chlorobenzene and mixtures thereof.

25. The process of claim 24 wherein said solvent is selected from the group consisting of nitrobenzene, N-methyl-2-pyrrolidone, pyridine, dimethylsulfoxide, dimethylformamide and toluene.

26. The process of claim 24 wherein said suitable solvent system includes a protic solvent.

27. The process of claim 26 wherein said protic solvent is selected from the group consisting of methanol, water and mixtures thereof.

28. The process of claim 21 wherein the molar ratio of said protic material to said suitable base is 0:1 to about 5:1 and the molar ratio of said suitable base to said aliphatic amine or substituted aliphatic amine derivative is about 1:1 to about 10:1.

29. The process of claim 21 wherein said suitable temperature is from about 10° C. to about 150° C.

30. The process of claim 21 wherein said suitable base is selected from the group consisting of organic and inorganic bases.

31. The process of claim 30 wherein said organic and inorganic bases are selected from the group consisting of alkali metals, alkali metal hydrides, alkali metal hydroxides, alkali metal alkoxides, phase transfer catalyst in conjunction with a base source, amines, crown ethers in conjunction with a base source, alkyl magnesium halides, and mixtures thereof.

32. The process of claim 21 wherein said base is selected from the group consisting of an aryl ammonium, alkyl ammonium, aryl/alkyl ammonium and alkyl diammonium salt in conjunction with a base source.

33. The process of claim 21 wherein said base is combined with said aliphatic amine or substituted aliphatic amine derivative to form a mixture, which mixture is then contacted with nitrobenzene.

34. The process of claim 21 wherein said aliphatic amine or substituted aliphatic amine derivative and nitrobenzene are contacted to form a mixture to which said base is added.

35. The process of claim 21 wherein said solvent is nitrobenzene and said base is a tetraalkyl ammonium hydroxide.

36. The process of claim 21 wherein said aliphatic amine or substituted aliphatic amine derivative and nitrobenzene are reacted under aerobic conditions.

37. The process of claim 22 wherein said aliphatic amine or substituted aliphatic amine derivative is represented by the formula X—R—NH₂ and said aliphatic amine or substituted aliphatic amine derivative and nitrobenzene are reacted under anaerobic conditions.

38. The process of claim 21 wherein a desiccant is present during step (b) to control the amount of protic material present during the reaction of aliphatic amine or substituted aliphatic amine derivative and nitrobenzene.

39. The process of claim 38 wherein said desiccant is selected from the group consisting of anhydrous sodium sulfate, molecular sieves, calcium chloride, tetramethylammonium hydroxide dihydrate, anhydrous potassium hydroxide, anhydrous sodium hydroxide and activated alumina.

40. The process of claim 21 wherein the amount of protic material in step (b) is controlled by the continuous distillation of said protic material.

41. The process of claim 21 further comprising:
   (d) reductively alkylating the N-aliphatic substituted p-phenylenediamine to produce N'-alkylated, N-aliphatic substituted p-phenylenediamine.

42. The process of claim 41 wherein said N-aliphatic substituted p-phenylenediamine is reductively alkylated utilizing a compound selected from the group consisting of ketones and aldehydes.

43. A process for preparing N'-alkylated, N-aliphatic substituted p-phenylenediamine comprising:
   (a) contacting an aliphatic amine or substituted aliphatic amine derivative and nitrobenzene in the presence of a suitable solvent system,
   (b) reacting the aliphatic amine or substituted aliphatic amine derivative and nitrobenzene in the presence of a suitable base and a controlled amount of protic material at a suitable temperature in a confined reaction zone, and
   (c) reductively alkylating the reaction product of (b) to produce N'-alkylated, N-aliphatic substituted p-phenylenediamine.

44. The process of claim 43 wherein said aliphatic amine and said substituted aliphatic amine derivative are selected from the group consisting of compounds having the formula X—R—NH—R'—Y and compounds having the formula:

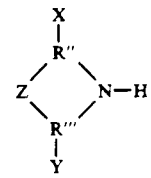

wherein R is selected from the group consisting of alkylene, alkenylene, cycloalkylene and cycloalkenylene groups, R' is selected from the group consisting of a direct bond, alkylene, alkenylene, cycloalkylene and cycloalkenylene groups, R" and R''' are independently selected from the group consisting of alkylene and alkenylene groups, Z is selected from the group consisting of a direct bond, —NH—, —N(R₁)—, —O— and S—, and X and Y are independently selected from the group consisting of hydrogen, halides, —NO₂, —NH₂, aryl groups, alkoxy groups, —SO₃R₁, —SO₃H, —OH, —COH, —COOH, and alkyl, aryl, arylalkyl or alkylaryl groups containing at least one —NH₂ group, wherein R₁ is an alkyl group and halides are selected from the group consisting of chloride, bromide and fluoride.

45. The process of claim 44 wherein said aliphatic amine and said substituted aliphatic amine derivatives are selected from the group consisting of cyclohexylamine, 2-butylamine, isopropylamine, 2-hexylamine, 2-heptylamine, 1,4-dimethylpentylamine, 1-methylheptylamine, 1-ethyl-3-methylpentylamine, 1,3-dimethylbutylamine, octylamine, piperidine, piperazine, 2-amino-1-propanol, 2-amino-1-butanol, hexamethylenediamine and 6-amino-hexanoic acid.

46. The process of claim 43 wherein said suitable solvent system includes a solvent selected from the group consisting of nitrobenzene, aliphatic amine, dimethylsulfoxide, dimethylformamide, N-methyl-2-pyrrolidone, pyridine, toluene, hexane, ethyleneglycoldimethylether, diisopropylethylamine, chlorobenzene and mixtures thereof.

47. The process of claim 46 wherein said solvent is selected from the group consisting of nitrobenzene, N-methyl-2-pyrrolidone, pyridine, dimethylsulfoxide, dimethylformamide and toluene.

48. The process of claim 46 wherein said suitable solvent system includes a protic solvent.

49. The process of claim 48 wherein said protic solvent is selected from the group consisting of methanol, water and mixtures thereof.

50. The process of claim 43 wherein the molar ratio of said protic material to said suitable base is 0:1 to about 5:1 and the molar ratio of said suitable base to said aliphatic amine or substituted aliphatic amine derivative is about 1:1 to about 10:1.

51. The process of claim 43 wherein said suitable temperature is from about 10° C. to about 150° C.

52. The process of claim 43 wherein said suitable base is selected from the group consisting of organic and inorganic bases.

53. The process of claim 52 wherein said organic and inorganic bases are selected from the group consisting of alkali metals, alkali metal hydrides, alkali metal hydroxides, alkali metal alkoxides, phase transfer catalyst in conjunction with a base source, amines, crown ethers in conjunction with a base source, alkyl magnesium halides, and mixtures thereof.

54. The process of claim 43 wherein said base is selected from the group consisting of an aryl ammonium, alkyl ammonium, aryl/alkyl ammonium and alkyl diammonium salt in conjunction with a base source.

55. The process of claim 43 wherein said base is combined with said aliphatic amine or substituted aliphatic amine derivative to form a mixture, which mixture is then contacted with nitrobenzene.

56. The process of claim 43 wherein said aliphatic amine or substituted aliphatic amine derivative and nitrobenzene are contacted to form a mixture to which said base is added.

57. The process of claim 43 wherein said solvent is nitrobenzene and said base is a tetraalkyl ammonium hydroxide.

58. The process of claim 43 wherein said aliphatic amine or substituted aliphatic amine derivative and nitrobenzene are reacted under aerobic conditions.

59. The process of claim 44 wherein said aliphatic amine or substituted aliphatic amine derivative is represented by the formula X—R—NH$_2$ and said aliphatic amine or substituted aliphatic amine derivative and nitrobenzene are reacted under anaerobic conditions.

60. The process of claim 43 wherein a desiccant is present during step (b) to control the amount of protic material present during the reaction of aliphatic amine or substituted aliphatic amine derivative and nitrobenzene.

61. The process of claim 60 wherein said desiccant is selected from the group consisting of anhydrous sodium sulfate, molecular sieves, calcium chloride, tetramethylammonium hydroxide dihydrate, anhydrous potassium hydroxide, anhydrous sodium hydroxide and activated alumina.

62. The process of claim 43 wherein the amount of protic material in step (b) is controlled by the continuous distillation of said protic material.

63. The process of claim 43 wherein said N-aliphatic substituted p-phenylenediamine is reductively alkylated utilizing a compound selected from the group consisting of ketones and aldehydes.

64. The process of claim 1 wherein said aliphatic amine or substituted aliphatic amine derivative is a primary amine represented by the formula X—R—NH$_2$ wherein X is selected from the group consisting of hydrogen, halides, —NO$_2$, —NH$_2$, aryl groups, alkoxy groups, —SO$_3$R$_1$, —SO$_3$H, —OH, —COH, —COOH, and alkyl, aryl, arylalkyl or alkylaryl groups having at least one —NH$_2$ group and R is selected from the group consisting of alkylene, alkenylene, cycloalkylene and cycloalkenylene groups, wherein R$_1$ is an alkyl group and halides are selected from the group consisting of chloride, bromide and fluoride.

65. The process of claim 21 wherein said aliphatic amine of substituted aliphatic amine derivative is a primary amine represented by the formula X—R—NH$_2$ wherein X is selected from the group consisting of hydrogen, halides, —NO$_2$, —NH$_2$, aryl groups, alkoxy groups, —SO$_3$R$_1$, —SO$_3$H, —OH, —COH, —COOH, and alkyl, aryl, arylalkyl or alkylaryl groups having at least one —NH$_2$ group and R is selected from the group consisting of alkylene, alkenylene, cycloalkylene and cycloalkenylene groups, wherein R$_1$ is an alkyl group and halides are selected from the group consisting of chloride, bromide and fluoride.

66. The process of claim 43 wherein said aliphatic amine or substituted aliphatic amine derivative is a primary amine represented by the formula X—R—NH$_2$ wherein X is selected from the group consisting of hydrogen, halides, —NO$_2$, —NH$_2$, aryl groups, alkoxy groups, —SO$_3$R$_1$, —SO$_3$H, —OH, —COH, —COOH, and alkyl, aryl, arylalkyl or alkylaryl groups having at least one —NH$_2$ group and R is selected from the group consisting of alkylene, alkenylene, cycloalkylene and cycloalkenylene groups, wherein R$_1$ is an alkyl group and halides are selected from the group consisting of chloride, bromide and fluoride.

* * * * *